(12) United States Patent
Morris et al.

(10) Patent No.: US 6,548,822 B1
(45) Date of Patent: Apr. 15, 2003

(54) METHOD OF PERFORMING ANALYTICAL SERVICES

(75) Inventors: John Steven Morris, Columbia, MO (US); Edward Allen Deutsch, Columbia, MO (US)

(73) Assignee: Curators of University of Missouri, Columbia, MO (US)

( * ) Notice: Subject to any disclaimer, the term of this patent is extended or adjusted under 35 U.S.C. 154(b) by 100 days.

(21) Appl. No.: 09/737,703

(22) Filed: Dec. 15, 2000

Related U.S. Application Data
(60) Provisional application No. 60/173,825, filed on Dec. 30, 1999.

(51) Int. Cl.[7] ............................................. G01N 15/16
(52) U.S. Cl. ...................................... 250/573; 250/288
(58) Field of Search ................................ 250/573, 282, 250/288

(56) References Cited

U.S. PATENT DOCUMENTS

| | | | | |
|---|---|---|---|---|
| 4,080,168 A | * | 3/1978 | Abu-Samra et al. | 23/230 R |
| 5,212,393 A | * | 5/1993 | Togawa et al. | 250/573 |
| 5,837,275 A | * | 11/1998 | Burrell et al. | 424/409 |
| 6,225,634 B1 | * | 5/2001 | Atrashkewivich et al. | 250/393 |
| 6,328,700 B1 | * | 12/2001 | Rheinhardt et al. | 600/504 |

* cited by examiner

*Primary Examiner*—Huy Mai
(74) *Attorney, Agent, or Firm*—Armstrong Teasdale LLP

(57) ABSTRACT

A method of determining providing analytical services, particularly trace element analysis is disclosed. The method includes supplying a sample container to a customer, having the customer return the sample container with the sample inside the container, and analyzing the sample by neutron activation analysis without opening the sample container.

43 Claims, 1 Drawing Sheet

METHOD OF PERFORMING ANALYTICAL SERVICES

CROSS REFERENCE TO RELATED APPLICATION

This application claims the benefit of U.S. Provisional Application No. 60/173,825, filed Dec. 30, 1999.

1. Field of the Invention

The present invention relates to analysis of trace elements, and more particularly a way of providing analytical services.

2. Background of the Invention

Trace elements play a role in health and nutrition that is being increasingly appreciated. A number of chemical elements that previously were thought not to have any biological role are now known to be crucial to the proper functioning of the metabolism. A prime example of such an element is cobalt, which is now known to be essential because of its role as a cofactor in vitamin $B_{12}$. Another trace element whose importance has only recently come to be appreciated is selenium.

For many vitamins, minerals, some trace elements and macro components of the diet such as fat, protein and carbohydrates intakes can be accurately estimated using state-of-the-art food-frequency questionnaires when administered and analyzed by experienced epidemiologists. However, because the needed quantity of selenium in the human diet is low, and selenium varies greatly in concentration among the same foods, selenium intake cannot be accurately estimated by food-frequency questionnaires in diverse human diets such as those in the U.S.

In addition to essential trace elements, trace elements can also be important because of their toxic effects. Numerous chemical elements that appear in minute quantities in the body but do not have a natural role can exert toxic effects if their levels become excessive. An example of such an element would be lead.

Thus knowledge of the concentration of trace elements in biological materials is desirable. Previous efforts to monitor trace elements have significant disadvantages. Most analytical methods, such as atomic absorption or emission spectroscopy, require extensive sample treatment before determination to obtain a homogenous sample before the determination can be carried out. Such treatment typically involves pulverizing, blending, or other mechanical disruption of the physical structure of the sample, followed by chemical digestion with corrosive acid, alkali, and/or oxidizing agents, to obtain a homogeneous sample. Sample treatment is tedious, time-consuming, and expensive, because it requires the services of a trained technician. Furthermore, the corrosive reagents pose a hazard to the technician, and the disposal of the spent reagents can be expensive if environmental damage is to be avoided.

These factors make analyses for trace elements expensive. Industries that must perform such analyses routinely commonly contract with outside analytical laboratories to have them done, or alternatively buy the instruments and hire technicians to do them in-house. Neither of these options is practical for small-time users of analytical services. The capital outlay to buy the instrumentation can hardly be economic for such users. Contracting with an outside laboratory can also be cost-prohibitive, particularly if the trace element to be determined is not one that is done routinely by that laboratory.

Thus there is a need for a way to provide fast, accurate, and inexpensive analyses to those in need of them, where the analyses involve as little sample preparation as possible, and where to streamline workflow the analytical method is virtually the same for a wide variety of elements.

Neutron activation analysis (NAA) is an attractive possibility, because it entails minimal sample preparation and has previously been used for analysis of a variety of materials, including toenail samples for selenium. Thus far, however, neutron activation analysis has seen little use for routine analytical determinations because of its unavailability to users that do not have a significant amount of work to be done. On one hand, because it requires access to a research nuclear reactor and to sophisticated emissions counting equipment, neutron activation analysis has been far beyond the capability of the average analytical laboratory. On the other hand, analysis of the occasional sample for a user would be uneconomic for the operators of a research reactor. Thus there is a need for a way to provide neutron activation analysis of trace elements to users in an inexpensive and cost-effective manner.

SUMMARY OF THE INVENTION

The present invention provides a way to offer analytical services, and more specifically trace element determinations, to users in an economic fashion by streamlining workflow and thereby maximizing sample throughput. It provides for sending prospective customers sample containers that have known weight, and that bear identifying indicia. The customer then places a sample of the material to be tested into the container and returns the container with the sample to the provider of analytical services. The provider identifies and weighs the container, and by comparison with the original weight determines the weight of the sample contained therein. The provider then places the filled sample container in a neutron flux, whereby elements in the sample are activated and emit radiation characteristic of the elements that absorbed the neutrons. By measuring the emitted radiation the provider can then determine the weight percentage of one or more elements in the sample in a fashion well-known to those of ordinary skill in the art. The provider then communicates the results of the analysis to the customer by ordinary mail, email, fax, Internet website, or other method.

DETAILED DESCRIPTION OF THE INVENTION

Definitions

Figure 1:
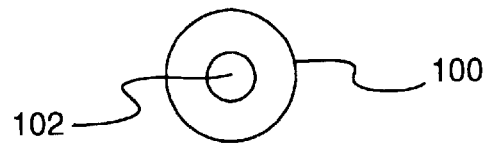
FIG. 1 shows a top view of a sample container with a laser access hole.

"Biological materials" as used herein means any material derived from a biological source, including but not limited to toenails, fingernails, hair, horn, hooves, cells from cheek scrapings, skin, teeth, excreta, tissue samples, such as those taken in biopsies or other medical or veterinary procedures, whether from humans or animals, and also includes leaves, roots, stems, flowers from plants, and foodstuffs derived from animals or plants.

"Geological and environmental materials" as used herein means any material extracted from the earth, including but not limited to rocks, minerals, ores, gems, soil, clay, mining samples, core samples, coal, oil, natural gas, surface water, ground water, rain water, and air.

Selenium is now recognized as an essential element for human and animal nutrition, where it plays an important role in anti-oxidants that mitigate free radical damage to body constituents. Selenium deficiency is associated or suspected of being associated with other serious pathologies, such as cancer, heart disease, and the progress of viral diseases such as HIV infection. Recognition of selenium's role in resisting such diseases has prompted consumers to take selenium dietary supplements, but such supplements are themselves a cause for concern because selenium exerts toxic effects at concentrations only modestly higher than those required by the body. This narrow window between selenium deficiency and selenium overload makes monitoring selenium levels in the body crucial.

Selenium is one of the more difficult of the trace elements to measure in biological samples. For most methods, accurate measurement of the selenium concentration requires that the sample be digested in oxidizing acids, which can result in volatilization losses. These procedures are time-consuming, require specialized equipment, and have high labor and materials costs.

Neutron activation analysis provides an attractive alternative to these wet chemical methods. It entails exposure of a sample to low-energy neutrons, usually produced by U-235 fission in a research reactor, whereby individual nuclides capture neutrons according to their energy-dependent cross sections. In many cases the result is a neutron-rich radionuclide that decays by the emission of an electron from the nucleus (beta decay) achieving greater stability by converting a neutron into a proton. Frequently this nuclear process results in an intermediate excited state that instantaneously decays by the emission of a photon that can be uniquely identified by its energy and quantitatively measured using high-resolution gamma-ray spectroscopy for both measurements. These quantitative measurements provide the basis for determination of an element by neutron activation analysis.

Neutron activation analysis (NAA) is performed by specific techniques called instrumental neutron activation analysis (INAA), chemical neutron activation analysis (CNAA), radiochemical neutron activation analysis (RNAA), prompt-gamma neutron activation analysis, epi-thermal neutron activation analysis, and fast neutron activation analysis. With the exception of prompt-gamma neutron activation analysis (PGNAA) neutron activation analysis consists of (1) neutron irradiation, (2) post-irradiation decay and (3) radiation detection (almost always this is done by high-resolution gamma-ray spectroscopy. For instrumental neutron activation analysis (INAA), these three steps are done on the sample that is generally analyzed as received with no chemical preparation. The sample may be dried or homogenized by various well-known procedures, after which it is either massed or volumetrically transferred to a suitable container for the neutron irradiation.

Chemical NAA entails chemical separation of the analyte (s) of interest from the bulk sample matrix prior to irradiation. This pre-irradiation preparation obviates one of the most important advantages of NAA, namely, avoiding contamination during sample preparation. CNAA is useful in those cases where the bulk matrix interferes prohibitively and the induced radionuclide that must be measured has a half-life too short to allow decay to reduce the interferences. Derivative NAA, a variant of CNAA, involves stoichiometric derivatization of the analyte of interest, which cannot otherwise be measured via NAA, with an element that can be analyzed via INAA. The surrogate is quantified and the analyte is computed from the gravimetric factor.

Radiochemical NAA employs chemical separation post-irradiation, which greatly improves both sensitivity and selectivity and makes full use of the unique advantage of NAA as an instrumental analysis technique because it does not require real-time measurement of the excitation signal. Under RNAA, the sample is irradiated and then generally dissolved via acid digestion or a fusion process. Addition of a carrier of the analyte element allows stoichiometric separation of the analyte from the bulk matrix, and the sample is then counted. Finally, a chemical yield is measured by any one of several well-known methods.

Epi-thermal and fast-NAA are both variants of INAA. In epi-INAA, the thermal neutrons are filtered out and the activation is limited to resonance neutrons. Fast-NAA is analogous to epi-INAA except it uses fast neutrons and instead of radiative capture, one looks at nuclear transitions of the nucleus whereby particles are emitted. For example phosphorus can be analyzed by P-31 (n, alpha) Al-28 where the n is a high-energy (fast) neutron>1 MeV.

For PGNAA, one measures the gamma ray emitted at the time of neutron capture. PGNAA is, therefore, a real-time technique; the sample must be placed in a neutron beam adjacent to the detector, which cannot be done in a high-flux position close to the core. Consequently, the neutron flux is lower by five orders of magnitude than for INAA, with corresponding reduction in sensitivity. PGNAA is used primarily in specialized cases, such as boron and cadmium, that have very large neutron-capture cross-sections.

Selenium has six stable nuclides, of which Se-74 and Se-76 are typically used to quantify selenium by neutron activation analysis. By comparison, the other selenium isotopes have less favorable neutron cross sections or gamma-ray parameters. While Se-74 offers excellent sensitivity, it requires long neutron irradiation and gamma-ray measurement times, which limits analytical sample throughput. Consequently, for research reactors having high neutron flux densities and fast pneumatic tubes use of Se-76 for the determination of selenium is more attractive. Most biological samples can be analyzed as received at a rate of approximately 1 per minute using the method described below.

Biological samples are weighed as received into pre-cleaned polyethylene vials. These vials are then placed in shuttle capsules and irradiated. At the time of neutron capture a compound nucleus is formed that immediately emits energy as photon emissions to achieve a more stable state. These so-called prompt gamma-rays must be measured in real time during neutron capture, which requires specialized instrumentation and does not have adequate sensitivity to quantify most elements, including selenium, in biological samples of interest. In most NAA experiments the decay gamma rays are measured as is done in this case. Because of Se-76's high neutron cross-section and the short Se-77 m half-life, the measurement time needed to accurately measure selenium in biological tissues is approximately 30 seconds. The 162 keV gamma ray is measured and selenium concentrations are determined by standard comparison.

Selenium distributes in mammalian tissues and fluids according to the biochemical requirements of the selenoproteins, with excess selenium eliminated largely in the urine. The ideal biologic monitor for assessment of selenium status should be functional over a wide range, integrate intake over a representative period, and be easy and affordable to collect, ship and store. It should also be capable of ready and accurate analysis, and should allow for assessment of other nutrients, interacting moieties, and toxic or infectious agents that may confound the assessment of selenium status. Whole blood, plasma, serum, urine, hair, nails and biopsied tissue have all been used for measurement of selenium concentrations in vivo, as has selenium-dependent glutathione peroxidase activity in blood products and some tissues.

Blood samples represent the usual way to obtain a tissue sample from those with acute selenium deficiency or overload, but for broader screening of the population blood samples are impractical. Besides requiring the intervention of a trained medical practitioner, they also reflect the patient's selenium status over a short period, specifically the preceding few days, and thus do not accurately reflect the patient's overall selenium status. Consequently, especially for large population-based screening studies, where perishable samples are tedious and expensive to collect and store, nails have emerged as the most useful source of tissue samples.

Selenium is absorbed from foods and incorporated in nails through protein synthesis. Specifically, the dry mass of nails is almost entirely α-keratin that includes approximately 15% in cystine cross links in addition to the cysteine contained in the helical keratin backbone. Seleno-cysteine is incorporated by substituting for the analogous amino acid; therefore selenium appears in the nail in relation to its concentration in the diet.

For most subjects, fingernails are slightly higher in their selenium concentration and appear to be more responsive to changes in Se intake compared to toenails. A larger fraction of the population is willing to provide a toenail specimen, however, and because toenails are environmentally sheltered in many populations, they are less likely to be externally contaminated. Also, a larger toenail sample is generally obtained. For these reasons, toenails have emerged as the preferred dietary monitor for selenium; and a spectrum of experimental data now exists quantitatively linking selenium intake to the measured toenail selenium concentration.

We have collected selenium concentration data on toenail specimens from subjects with known selenium intakes and found that the toenail selenium concentration can be related to dietary intake by the equation $I_{150\ lb} = k_2 \times T^2 + k_1 \times T + k_0$, where $I_{150\ lb}$ is the selenium intake (in μg/day) from food for a 150 pound person, T is the toenail Se concentration (ppm by weight), and $k_0$, $k_1$, and $k_2$ are constants. This quadratic model applies to the intake of selenium from foods, from which the body absorbs selenium with greater efficiency than from supplements. To estimate total selenium intake from both food and supplements, the model must be expanded by accounting for use of Se supplements because selenium is with different efficiency from dietary supplements than from the diet. The methodology is first to inquire about Se supplement use, then from a gender-specific model independently determined to calculate and subtract from the total the fraction of the toenail selenium concentration that is due to supplements, and last, from the difference, to estimate dietary Se through use of the quadratic model. We have found that selenium intake from both dietary supplements as well as from diet can be estimated from the selenium concentration in toenails through use of the equation $I_{150\ lb} = Se_{diet} + Se_{supplement} = [k_2(T - S \times f_g)^2 + k_1(T - S \times f_g) + k_0] + S$, where $Se_{diet}$ is the selenium intake (in μg/day) from the diet, $Se_{supplement}$ is the selenium intake (in μg/day) from dietary supplements, $I_{150\ lb}$ is the selenium intake (in μg/day) from both food and dietary supplements, all for a 150 pound person, T is the toenail Se concentration (ppm by weight), S is the amount of selenium taken in dietary supplements (in μg/day), $k_0$, $k_1$, and $k_2$ are constants, and $f_g$ is a gender-specific supplement regression factor.

The provider of analytical services distributes to prospective customers, optionally for a fee, a sample container into which the customer places a sample of interest. The sample container preferably is a cylindrical vial made of high-purity glass, quartz, and plastic, and more preferably is made of a plastic selected from the group consisting of polyethylene, polypropylene, polycarbonate, polystyrene, nylon, and polyacrylate. Other materials may be used, however, as will be appreciated by those skilled in the art. Similarly, neither the shape nor the dimensions of the sample container are critical. The sample container can have a variety of shapes, including without limitation rectangular prismatic, triangular, and ellipsoidal. Further, to help position the sample within the container, the sample container can optionally contain a compressible spacer material that is substantially free of the trace element of interest, and that therefore does not substantially interfere with the analysis. In a preferred embodiment expanded polyethylene is used, but other materials that do not interfere with the analysis can be used.

The sample container comprises two portions, a sample-holding portion, and a cap that substantially closes the sample-holding portion when the cap is in place, so that the sample is held securely within the container. The cap engages the sample-holding portion by friction, by threads, by a fastener, or by other methods well known to those skilled in the art of packaging. The sample container is weighed, the weight recorded, and the container given a unique identifier before being supplied to the customer. The unique identifier can be, without limitation, a label, a bar code, a laser-engraved identifier, or other identifier well known to those skilled in the relevant art. The above description is illustrative and is not to be construed as limiting the invention.

On receiving the sample container, the customer places within it the sample of interest, replaces the cap, and returns the sample container to the provider of analytical services. On receiving the filled sample container the provider of analytical services determines the weight and the identifier of the container, and thereby determines the weight of the sample. The provider then places the sample container in a neutron flux of appropriate energy and fluence to activate nuclei of the element of interest in the sample. Following neutron activation, the provider then counts emissions from the activated nuclei of interest in the fashion well known to those skilled in the art of neutron activation analysis. The provider then relates the emissions count to the amount of the element of interest in the sample, and determines the weight percent of that element in the sample by calculating the ratio of the weight of the element of interest to the weight of the sample. The provider reports the weight percent of the element in the sample to the customer by, without limitation, telephone, paper mail, facsimile transmission, telegraph, email, or making the results available over the Internet.

The inventive method can also be used to provide a calibration for other analytical methods. Laser-ablation inductively-coupled plasma mass spectrometry is one such method, wherein a laser is directed across the surface of a sample to ablate its surface by vaporizing it. Laser ablation in conjunction with inductively-coupled mass spectrometry (ICP-MS) provides a way of selectively vaporizing and then analyzing the surface of a sample, through analysis by the well-known method of ICP-MS. Laser-ablation inductively-coupled-plasma mass spectrometry (LA-ICP-MS) offers the advantage of providing the spatial distribution in the sample of the element to be analyzed, which in the case of hair or a nail can be related to the temporal profile. Adoption of LA-ICP-MS has been hindered by the relative nature of the analytical determination it yields; the need to provide an internal standard requires sample manipulation that obviates the intrinsically high throughput, minimal intervention nature of the method. Use of the neutron activation analysis of the inventive method in conjunction with LA-ICP-MS solves this problem. Neutron activation analysis affords an absolute determination of an element, which can be used as a calibration standard for determination of the same or other elements by LA-ICP-MS. In the former case, LA-ICP-MS can be used to determine the spatial distribution of the element in a sample, which for biological materials such as nails can often be related to the temporal profile of exposure to that element.

Figure 2:
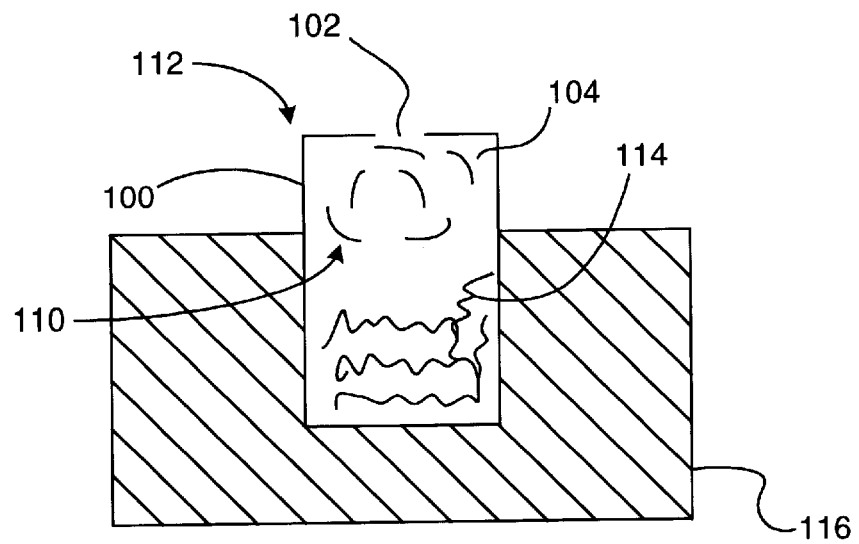
FIG. 2 shows a side view of the sample container shown in FIG. 1 having a laser access hole and positioned in a holder.
Figure 3:
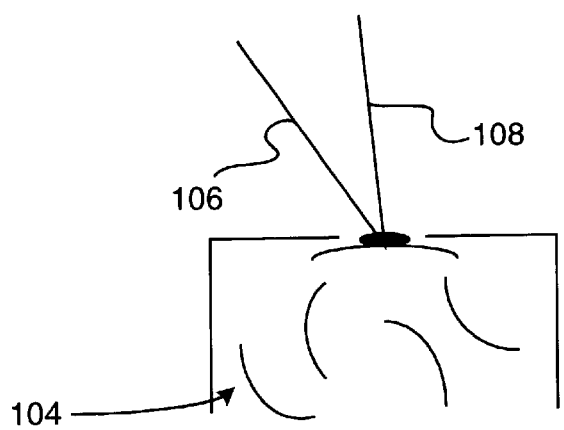
FIG. 3 shows an expanded side view of the sample container shown in FIG. 1 with a focusing laser beam and an incident laser ablation beam impinging on a sample within the sample container.

For an LA-ICP-MS sample container 100 has a port 102 to provide laser access to the sample 104, as shown in FIGS. 1–3. Two laser beams are commonly used for LA-ICP-MS, a low-power focusing laser beam 106 and a high-power ablation laser beam 108, as shown in FIG. 3, although only the high-power ablation laser beam is critical. Port 102 is adapted to accept the laser beams of the laser ablation system, whereby both laser beams 106 and 108 can be efficaciously swept across sample 104 contained within sample container 100. Port 102 can be either in a sample-holding portion 110 of container 100 or in a cap 112, and if sample container 100 is a cylindrical vial Port 102 can be either on an axis of the cylinder or perpendicular to it. In a preferred embodiment, port 102 is on the axis of the cylinder and is about 1 mm to about 2 mm in diameter, although those skilled in the relevant art will appreciate that the dimensions of port 102 are not critical. Sample container 100 optionally includes a mounting device 114 that positions at least part of sample 104 within port 102, whereby the laser beam can gain access to sample 104. Mounting device 114 is made of a material compatible with the laser chamber, where the criterion for compatibility is that the material not substantially absorb the laser beam. In an alternative embodiment, sample container 100 includes a compressible spacer material 116 below sample 104.

Besides selenium, other elements can also be determined by the inventive method because of the broad applicability of neutron activation analysis. Examples include other essential elements, such as zinc and molybdenum, and also toxic elements, such as arsenic and mercury. Elements with atomic number Z greater than 7 can generally be analyzed by neutron activation analysis, and optionally thereafter by LA-ICP-MS. In a preferred embodiment, elements with atomic number Z=8 to 42, 44 to 80, 88, 90, 92, and 93 are analyzed. In a more preferred embodiment, the element analyzed is selected from the group consisting of aluminum, antimony, arsenic, bromine, cadmium, calcium, chlorine, chromium, cobalt, copper, fluorine, gold, hafnium, iodine, iron, magnesium, manganese, mercury, molybdenum, nickel, platinum, potassium, scandium, selenium, silver, sodium, sulfur, thorium, tin, titanium, tungsten, uranium, vanadium, and zinc.

The inventive method can be used for a variety of biological materials. Instead of toenails, fingernails, hair, cells from cheek scrapings, skin, teeth, excreta, blood, tissue samples, and materials derived from them can be used, where materials derived from them include proteins and other biological components obtained by fractionation of the sample. Similarly, the biological materials need not be taken from humans, but can also be obtained from animals, both vertebrate and invertebrate, as well as plants. The method can thus be seen to have applications in veterinary medicine, animal husbandry, and agriculture, where trace element deficiencies can adversely affect crop yields.

Similarly, the inventive method can be used for non-biological materials, including in particular geological and environmental materials. Such materials include soil samples, rock samples, mining samples, drilling samples, and petroleum samples, surface water samples, deep water samples, rain water samples, sea water samples, and air samples. Further, the inventive method can be used for industrial materials, including materials used in the electronics and semiconductor industries, including in particular the group 13, 14, 15, and 16 elements such as silicon and germanium, gallium, indium, thallium, tin, lead, arsenic, antimony, bismuth, selenium, tellurium.

The foregoing description is intended to illustrate the aspects of the invention, and not to be limiting to it.

What is claimed is:

1. A method of performing analytical services, said method comprising the steps of:

supplying a sample container to a customer desirous of determining the concentration of a chemical element in a sample, having the customer place the sample in the sample container and return the sample for analysis, analyzing the sample by neutron activation analysis without opening the sample container, and reporting the results to the customer.

2. A method in accordance with claim 1 wherein the neutron activation analysis is performed by a method selected from the group consisting of instrumental neutron activation analysis, chemical neutron activation analysis, radiochemical neutron activation analysis, prompt-gamma neutron activation analysis, epi-thermal neutron activation analysis, and fast neutron activation analysis.

3. A method in accordance with claim 2 wherein the neutron activation analysis is performed by instrumental neutron activation analysis.

4. A method in accordance with claim 2 wherein neutron activation analysis of one element is used as an internal standard for analysis by laser-ablation inductively-coupled plasma mass spectrometry of a second element.

5. A method in accordance with claim 4 wherein analysis by neutron activation analysis and by laser-ablation inductively-coupled plasma mass spectrometry are performed without removing the sample from the sample container.

6. A method in accordance with claim 1 further comprising the step of analyzing the sample by laser-ablation inductively-coupled plasma mass spectrometry.

7. A method in accordance with claim 1 wherein the sample container is adapted for both instrumental neutron activation analysis and laser-ablation inductively-coupled plasma mass spectrometry.

8. A method in accordance with claim 1 wherein the sample container is a vial.

9. A method in accordance with claim 8 wherein the sample container is constructed from a material selected from the group consisting of glass, quartz, and plastic.

10. A method in accordance with claim 9 wherein the plastic is selected from the group consisting of polyethylene, polypropylene, polycarbonate, polystyrene, nylon, and polyacrylate.

11. A method in accordance with claim 8 wherein the sample container has a port to provide laser access to the sample.

12. A method in accordance claim 11 wherein the sample container includes a mounting device that positions at least part of the sample within the port, whereby the laser beam can gain access to the sample.

13. A method in accordance claim 1 wherein the sample container is given a unique identifier before it is supplied to the customer.

14. A method in accordance with claim 13 wherein the unique identified is a bar code.

15. A method in accordance with claim 13 wherein the unique identifier is a laser engraved identifier.

16. A method in accordance with claim 15 wherein the sampel container has been accurately weighed.

17. A method in accordance with claim 1 wherein the analysis is prepaid.

18. A method in accordance with claim 1 wherein the results are reported by a reporting method selected from the group consisting of email, fax, telephone, Internet website, and paper mail.

19. A method in accordance with claim 18 wherein the reporting method is email.

20. A method in accordance with claim 18 wherein the reporting method is an Internet website.

21. A method in accordance with claim 20 wherein the element is selenium.

22. A method in accordance with claim 1 wherein the analysis is an elemental analysis for elements selected from the group consisting of elements having an atomic number Z greater than 7.

23. A method in accordance with claim 22 wherein the elemental analysis is for elements selected from elements with atomic number Z=8 to 42, 44 to 80, 88, 90, 92, and 93.

24. A method in accordance with claim 22 wherein the element is selected from the group consisting of aluminum, antimony, arsenic, bromine, cadmium, calcium, chlorine, chromium, cobalt, copper, fluorine, gold, hafnium, iodine, iron, magnesium, manganese, mercury, molybdenum, nickel, platinum, potassium, scandium, selenium, silver, sodium, sulfur, thorium, tin, titanium, tungsten, uranium, vanadium, and zinc.

25. A method in accordance with claim 1 wherein the sample is selected from the group consisting of industrially made materials, biological materials, and geological and environmental materials.

26. A method in accordance with claim 25 wherein the industrially-made material comprises an element selected from the group consisting of elements from group 13, group 14, group 15, and group 16 of the periodic table.

27. A method in accordance with claim 26 wherein the industrially-made material comprises an element selected from the group consisting of gallium, indium, thallium, silicon, germanium, tin, lead arsenic, antimony, bismuth, sulfur, selenium, and tellurium.

28. A method in accordance with claim 27 wherein the industrially made material comprises an element selected from the group consisting of silicon and germanium.

29. A method in accordance with claim 27 wherein the industrially-made material comprises silicon.

30. A method in accordance with claim 25 wherein the biological material is taken from an organism selected from the group consisting of humans, animals, and plants.

31. A method in accordance with claim 30 wherein the biological sample is taken from a mammal.

32. A method in accordance with claim 31 wherein the biological sample is taken from a human.

33. A method in accordance with claim 32 wherein the biological sample is selected from the group consisting of toenails, fingernails, hair, cells from cheek scrapings, skin, teeth, excreta, blood, tissue samples, and materials derived from them.

34. A method in accordance with claim 33 wherein the sample is a nail selected from the group consisting of toenails and fingernails.

35. A method in accordance with claim 34 wherein said analysis comprises determining selenium intake through use of the relation $I_{150}$ lb=$k_2 \times T^2 + k_1 \times T + k_0$, wherein I is the intake in microgram of Se per day from food for a 150-pound person, T is the weight in milligrams of the nail, Se concentration is in ppm, and $k_0$, $k_1$, $k_2$ are constants.

36. A method in accordance with claim 34 wherein said analysis comprises determining selenium intake through use of the relation $I_{150}$ lb=$[k_2(T-S|\times|_{fg})2 + k_1(T-S|\times|_{fg}) + k_0] + S$ where $I_{150}$ lb is the selenium intake in $\mu$g/day from both food and dietary supplements for a 150 pound person, T is the toenail Se concentration in ppm by weight, S is the amount of selenium taken in dietary supplements in $\mu$g/day, $k_0$, $k_1$, and $k_2$ are constants, and fg is a gender-specific supplement regression factor.

37. A method in accordance with claim 33 wherein the sample is a toenail.

38. A method in accordance with claim 25 wherein the geological and environmental material is selected from the group consisting of soil samples, rock samples, mining samples, drilling samples, and petroleum samples.

39. A method in accordance with claim 25 wherein the environmental material is selected from the group consisting of surface water samples, deep water samples, rain water samples, and sea water samples.

40. A method in accordance with claim 1 further comprising the step of analyzing the sample by laser ablation-inductively-coupled plasma mass spectrometry.

41. A method in accordance with claim 40 wherein the analytical results from neutron activation analysis of an element are used as an absolute calibration for the analysis of the same or a different element by laser ablation-inductively-coupled plasma mass spectrometry.

42. A method in accordance with claim 40 wherein the species determined by laser ablation-inductively-coupled plasma-mass spectrometry is selected from the group consisting of selenium, chromium, aluminum, americium, antimony, arsenic, barium, beryllium, bismuth, boron, bromine, cadmium, calcium, californium, cerium, cesium, chlorine, chromium, cobalt, copper, dysprosium, erbium, europium, gadolinium, gallium, germanium, gold, hafnium, holmium, indium, iodine, iridium, iron, lanthanum, lead, lithium, lutetium, magnesium, manganese, mercury, molybdenum, neodymium, neptunium, nickel, niobium, osmium, palladium, phosphorus, platinum, plutonium, potassium, praseodymium, promethium, protactinium, radium, rhenium, rhodium rubidium, ruthenium, samarium, scandium, selenium, silicon, silver, sodium, strontium, sulfur, tantalum, technetium, tellurium, terbium, thallium, thorium, thulium, tin, titanium, tungsten, uranium, vanadium, ytterbium, yttrium, zinc, and zirconium.

43. A method in accordance with claim 42 wherein the species determined by laser ablation-inductively-coupled plasma-mass spectrometry is selected from the group consisting of aluminum, antimony, arsenic, boron, bromine, cadmium, calcium, chlorine, chromium, cobalt, copper, gold, hafnium, iodine, iron, lead, lithium, magnesium, manganese, mercury, molybdenum, nickel, phosphorus, plutonium, potassium, scandium, selenium, silicon, silver, sodium, strontium, sulfur, technetium, tellurium, thallium, thorium, tin, titanium, tungsten, uranium, vanadium, and zinc.

\* \* \* \* \*